US006910331B2

(12) United States Patent
Asai et al.

(10) Patent No.: US 6,910,331 B2
(45) Date of Patent: *Jun. 28, 2005

(54) STIRLING ENGINE

(75) Inventors: Masahiro Asai, Saitama (JP); Masaki Ban, Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 138 days.

This patent is subject to a terminal disclaimer.

(21) Appl. No.: 10/097,018

(22) Filed: Mar. 14, 2002

(65) Prior Publication Data

US 2002/0152750 A1 Oct. 24, 2002

(30) Foreign Application Priority Data

Mar. 14, 2001 (JP) ........................................ 2001-071796
Mar. 16, 2001 (JP) ........................................ 2001-075568

(51) Int. Cl.[7] .............................................. F01B 29/10
(52) U.S. Cl. ........................................ 60/517; 60/520
(58) Field of Search ........................ 60/517, 520, 526, 60/518, 522, 525

(56) References Cited

U.S. PATENT DOCUMENTS

| 4,454,426 | A | * | 6/1984 | Benson | 290/1 R |
|---|---|---|---|---|---|
| 5,022,229 | A | * | 6/1991 | Vitale | 62/6 |
| 5,174,116 | A | * | 12/1992 | Ishikawa | 60/520 |
| 5,394,700 | A | * | 3/1995 | Steele | 60/525 |
| 5,417,066 | A | * | 5/1995 | Kawano et al. | 60/517 |
| 5,873,246 | A | * | 2/1999 | Beale | 60/520 |
| 6,094,912 | A | * | 8/2000 | Williford | 60/520 |
| 6,543,216 | B2 | * | 4/2003 | Asai et al. | 60/39.6 |
| 6,645,252 | B2 | * | 11/2003 | Asai et al. | 623/24 |

* cited by examiner

Primary Examiner—Hoang Nguyen
(74) Attorney, Agent, or Firm—Birch, Stewart, Kolasch & Birch, LLP

(57) ABSTRACT

To provide a Stirling engine and a control unit for a Stirling engine capable of disposing a displacer unit and a power cylinder unit separately from each other, thereby increasing the degree of freedom of layout thereof. A displacer unit and a power cylinder unit of a Stirling engine E are disposed separately from each other. A compression chamber of the displacer unit is connected to an operation chamber of the power cylinder unit via a pressure conduit. A control actuator capable of arbitrarily controlling the displacer piston of the displacer unit is connected to the displacer piston.

9 Claims, 10 Drawing Sheets

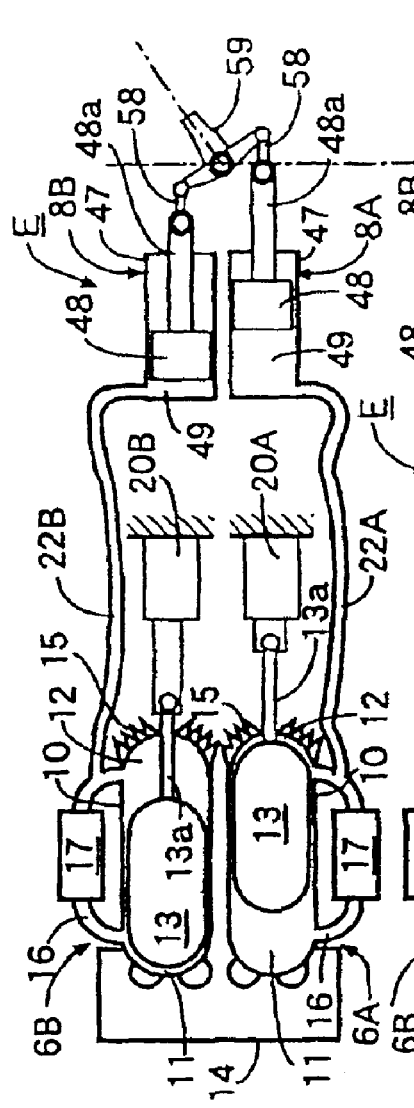
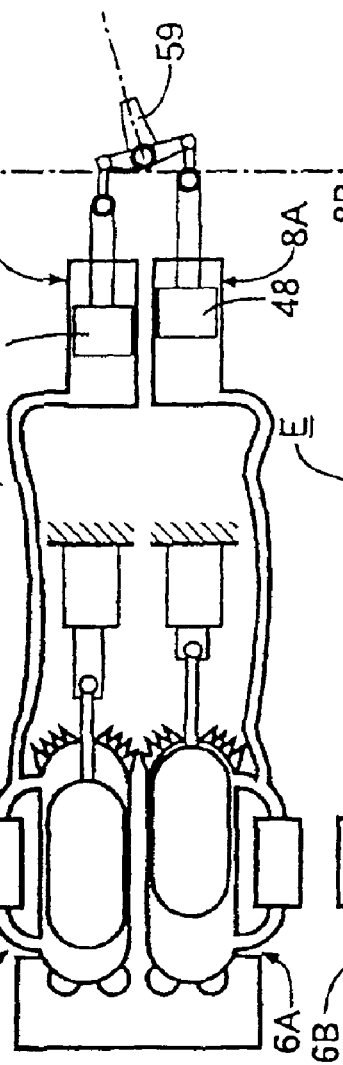
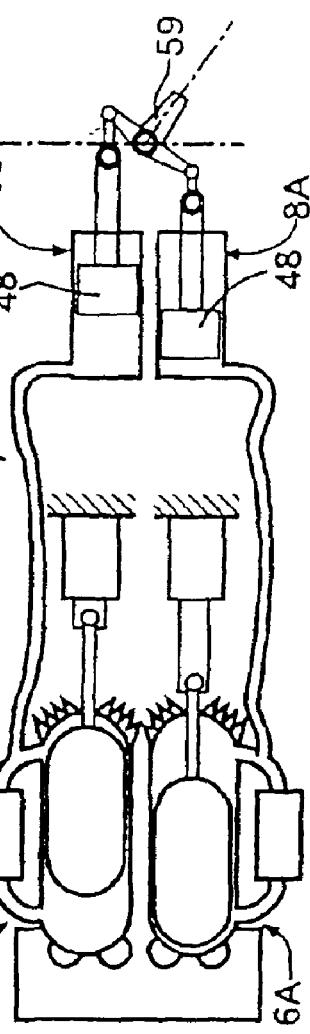
FIG. 12(a)
FIG. 12(b)
FIG. 12(c)

STIRLING ENGINE

CROSS-REFERENCE TO RELATED APPLICATIONS

The present application claims priority under 35 USC 119 to Japanese Patent Application Nos. 2001-071796 filed on Mar. 14, 2001 and 2001-075568 filed on Mar. 16, 2001 the entire contents thereof are hereby incorporated by reference.

1. Field of the Invention

The present invention relates to a Stirling engine and a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder.

2. Description of the Background Art

A Stirling engine is known as disclosed, for example, in a handbook entitled "Car Engineering Series, Vol. 8 'Electric Car, New Type Motor'" issued by SANKAIDO Publishing Co., Ltd.

The above-described Stirling engine has a problem that since a displacer cylinder and a power cylinder of the Stirling engine are integrated with each other, the engine is voluminous as a whole, with a result that in some applications, the degree of freedom in layout of the engine is reduced.

SUMMARY AND OBJECTS OF THE INVENTION

In view of the foregoing, the present invention has been made, and an object of the present invention is to provide a Stirling engine capable of disposing a displacer unit and a power cylinder unit separately from each other, and increasing the degree of freedom of layout of the engine, thereby enhancing the applicability of the engine.

In the above-described prior art Stirling engine, since a displacer piston and a power piston are mechanically connected to each other with a specific phase difference maintained therebetween, the phase of the power piston is uniquely determined by the phase of the displacer piston. Accordingly, since the motion control of the power piston of the prior art Stirling engine is performed only by adjusting heat generated by a heating portion of a displacer unit, the responsiveness of the motion control is significantly low, and therefore, the application of the prior art Stirling engine is limited to a power source of an apparatus in which a variation in load is relatively small.

In view of the foregoing, the present invention has been made, and an object of the present invention is to provide a control unit for a Stirling engine, which is capable of positively controlling the motion of a power piston with a high responsiveness and hence to improve the applicability of the Stirling engine.

To achieve the above object, according to a first feature of the present invention, there is provided a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder. The displacer unit and the power cylinder unit are disposed separately from each other. The compression chamber is connected to the operation chamber via a pressure conduit. A control actuator is capable of arbitrarily controlling the displacer piston and is connected to the displacer piston.

With the first feature, the displacer unit and the power cylinder unit can be disposed separately from each other, more specifically, freely disposed at desired positions. As a result, it is possible to increase the degree of freedom in layout of the Stirling engine and thereby to enhance the applicability of the Stirling engine. Further, the power piston of the power cylinder unit can be freely remote-controlled by controlling a phase and an operating speed of the displacer piston by means of the control actuator.

According to a second feature of the present invention, in addition to the first feature, the pressure conduit has flexibility. With this second feature, the displacer unit and the power cylinder unit can be displaced relative to each other by the flexibility of the pressure conduit, so that the displacer unit and the power cylinder unit can be disposed without interference therebetween. As a result, it is possible to further increase the degree of freedom in layout of the Stirling engine and hence to further enhance the applicability of the Stirling engine.

According to a third feature of the present invention, in addition to the first or second feature, a hydraulic converter for converting a pressure in the compression chamber to a hydraulic pressure and transmitting the hydraulic pressure to the operation chamber is provided between the compression chamber and the pressure conduit.

With this third feature, since a pressure in the compression chamber of the displacer unit is converted into a hydraulic pressure by the hydraulic converter and the hydraulic pressure is transmitted to the operation chamber, elastic compression, which is liable to occur in the case of using a working gas as a transmission medium, does not occur in both the pressure conduit and the operation chamber, so that it is possible to improve a pressure transmission efficiency. Further, since the pressure conduit is filled with a non-compressive fluid, it is possible to eliminate a possibility that an inner volume of the pressure conduit becomes a dead volume of the Stirling engine, and hence to improve a theoretical efficiency of the Stirling engine.

According to a fourth feature, there is provided a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder. The control system includes a displacer piston driving means for driving the displacer piston, a displacer piston position detecting means for detecting a position of the displacer piston, a power piston position detecting means for detecting a position of the power piston and a control unit for controlling an operation of the displacer driving means on the basis of detection signals from both piston position detecting means.

With this fourth feature, it is possible to control the motion of the power piston with a high responsiveness by operating the displacer piston at a suitable time by the displacer driving means, and hence to increase the applicability of the Stirling engine. In particular, since the operation of the displacer driving means is controlled by the control unit on the basis of a detection of signals from the displacer piston position detecting means and the power piston position detecting means, it is possible to freely control the operation, stoppage, an operating speed and a stopped position of the power piston irrespective of heat generated by the heating portion of the displacer unit.

According to a fifth feature of the present invention, the displacer piston driving means is operated by the control unit so as to change a difference in phase between the displacer piston and the power piston.

With this fifth feature, it is possible to freely control an operating timing and a stopping timing of the power piston.

According to a sixth feature of the present invention, there is provided a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder. The control system includes a displacer piston driving means for driving the displacer piston, a heat control means for controlling a heat generated by a heating portion of the displacer cylinder, a displacer piston position detecting means for detecting a position of the displacer piston, a power piston position detecting means for detecting a position of the power piston and a control unit for controlling an operation of the heat control means on the basis of detection signals from both piston position detecting means.

With this sixth feature, it is possible to control the motion of the power piston with a high responsiveness by operating the displacer piston at a suitable time by the displacer driving means, and hence to increase the applicability of the Stirling engine. In particular, since the operation of the heat control means for controlling heat generated by the heating portion of the displacer cylinder is controlled by the control unit on the basis of detection signals from the displacer piston position detecting means and the power piston position detecting means, it is possible to efficiently use heat generated by the heating portion.

According to a seventh feature of the present invention, there is provided a control system for a Stirling engine including a displacer unit in which a displacer piston is slidably fitted in a displacer cylinder so as to partition the inside of the cylinder into an expansion chamber and a compression chamber, and a power cylinder unit in which a power piston is slidably fitted in a power cylinder so as to form an operation chamber in communication with the compression chamber in the cylinder. The control system includes a displacer piston driving means for driving the displacer piston, a load adjusting means for adjusting a load of a load apparatus connected to the power piston, a displacer piston position detecting means for detecting a position of the displacer piston, a power piston position detecting means for detecting a position of the power piston and a control unit for controlling an operation of the load adjusting means on the basis of detection signals from both piston position detecting means.

With this seventh feature, it is possible to control the motion of the power piston with a high responsiveness by operating the displacer piston at a suitable time by the displacer driving means, and hence to increase the applicability of the Stirling engine. In particular, since the operation of the load adjusting means is controlled by the control unit on the basis of detection signals from the displacer piston position detecting means and the power piston position detecting means, it is possible to stabilize the output from the power piston even if the heat generated by the heating portion is somewhat varied.

The displacer driving means is equivalent to each of actuators 20, 20A and 20B to be described in embodiments of the present invention. The displacer piston position detecting means is equivalent to a displacer piston sensor 21. The power piston position detecting means is equivalent to a bending/stretching sensor 51 or a power piston sensor. The heat control means is equivalent to a fuel adjuster 44.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 12(*a*), 12(*b*) and 12(*c*) are vertical sectional views showing configurations of a Stirling engine according to a seventh embodiment of the present invention.

DETAILED DESCRIPTION OF THE PREFERRED EMBODIMENTS

Hereinafter, embodiments of the present invention will be described with reference to the accompanying drawings.

Figure 1:
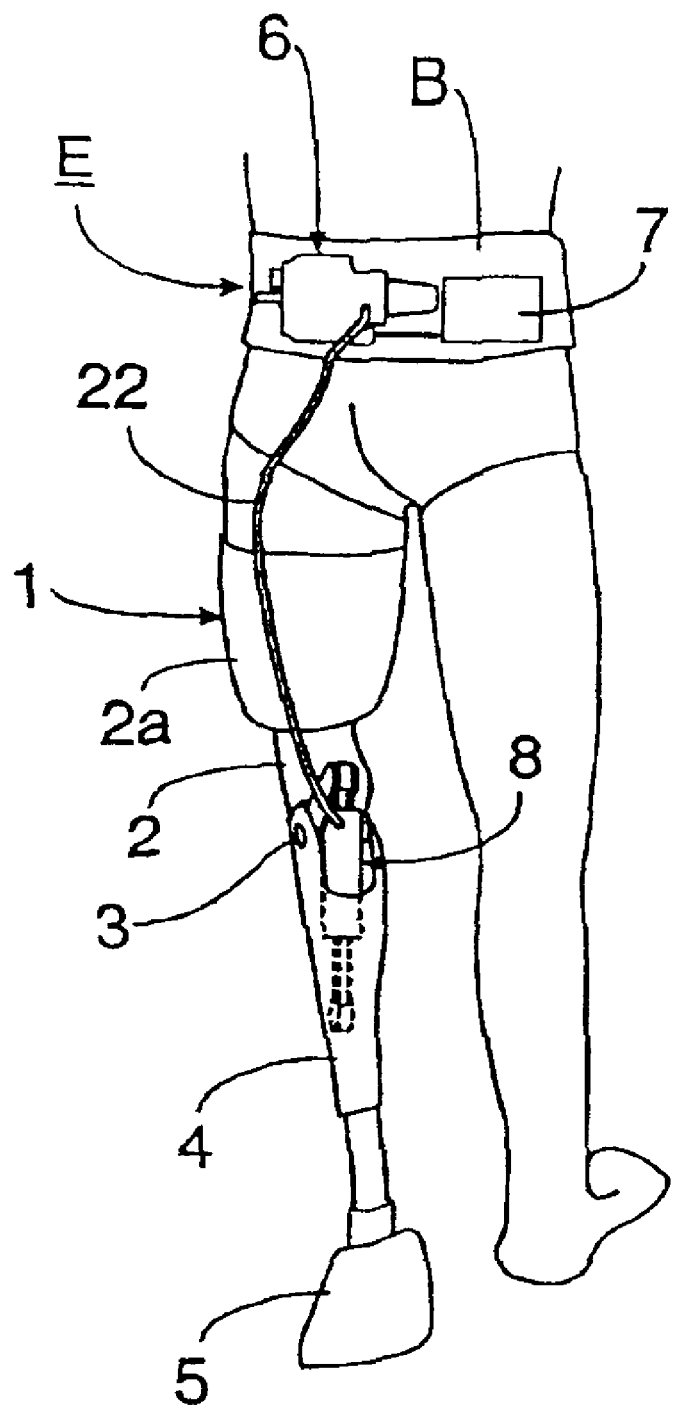
FIG. 1 is a rear view of a user wearing a drive unit for a prosthetic limb including a Stirling engine according to a first embodiment of the present invention.
Figure 2:
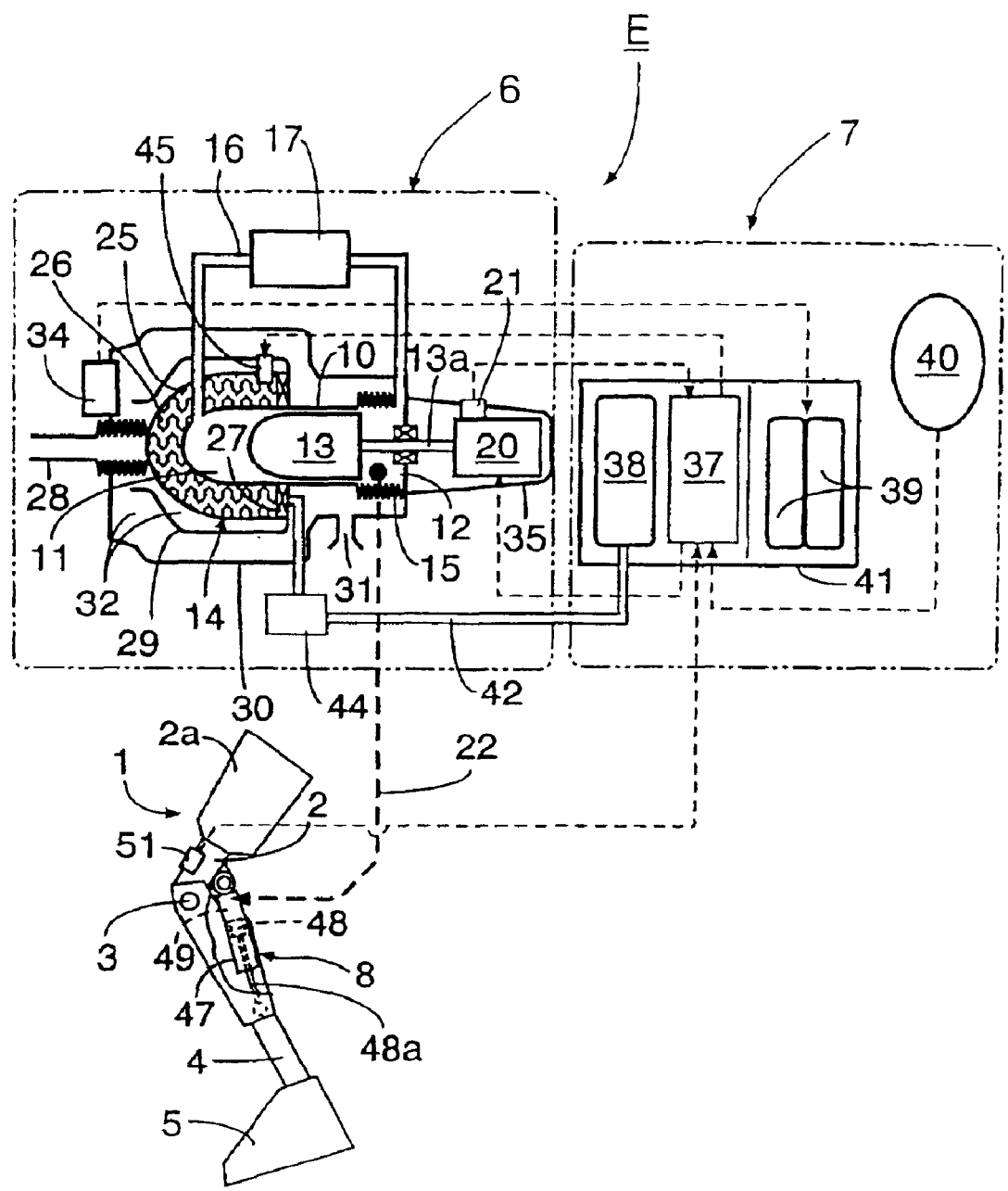
FIG. 2 is a vertical sectional view of the Stirling engine.

A first embodiment of the present invention shown in FIGS. 1 and 2 will be described below. In FIGS. 1 and 2, a Stirling engine E of the present invention is illustrated which is typically used for driving a prosthetic leg 1. The prosthetic leg 1 includes a thigh portion 2 integrated with a socket 2*a* in which a user's remaining thigh portion is to be inserted. A shank portion 4 is bendably/stretchably connected to a lower end of the thigh portion 2 via a joint 3. A foot portion 5 is connected to a lower end of the shank portion 4.

The Stirling engine E includes a displacer unit 6 and a control unit 7, which are mounted on a belt B worn around a user's waist portion. A power cylinder unit 8 is mounted on the prosthetic leg 1 at a position between the thigh portion 2 and the shank portion 4. A pressure conduit 22 is provided for transmitting a pressure generated in the displacer unit 6 to the power cylinder unit 8. A configuration of such a Stirling engine E will be more fully described with reference to FIG. 2.

The displacer unit 6 includes a displacer cylinder 10. A displacer piston 13 is slidably inserted in the cylinder 10 so as to partition the inside of the cylinder 10 into an expansion chamber 11 on a head side of the cylinder 10 and a compression chamber 12 on a bottom side of the cylinder 10. A combustor 14, provided around the head portion of the displacer cylinder 10, is provided for heating the expansion chamber 11. A radiator 15 is provided on the bottom portion of the displacer cylinder 10 for cooling the compression chamber 12. A heat regenerator 17 is interposed in a communication port 16 for connecting the expansion chamber 11 to the compression chamber 12. A motor-driven control actuator 20 is provided for driving the displacer piston 13 via a rod 13a passing through the bottom portion of the displacer cylinder 10. A displacer piston sensor 21 for detecting a position of the displacer piston 13 is provided on the control actuator 20.

The combustor 14 is of a catalyst type in which a combustion housing 25, formed on an outer surface of the head portion of the displacer cylinder 10, is filled with catalyst 26 for combustion. A fuel-air mixer 27 is provided at one end portion of the combustion housing 25 and an exhaust pipe 28 is provided at the other end of the housing 25.

A heat exchange wall 29 for covering the combustion housing 25 and a base portion of the exhaust pipe 28 is formed around the combustion housing 25. A shroud 30 for covering the heat exchange wall 29 is formed around the heat exchange wall 29. An air intake port 31, formed in the shroud 30, is in communication with an air inlet of the fuel-air mixer 27 via an air passage 32 meandering in each space between two of the combustion housing 25, the heat exchange wall 29, and the shroud 30.

A thermal-electric converting device 34 is additionally provided on the shroud 30 at a position near the heat exchange wall 29. The thermal-electric converting device 34 converts heat transferred from the heat exchange wall 29 into electricity, to charge a storage battery 39 with electricity. A supporting wall 35 for containing the control actuator 20 while supporting a fixed portion of the actuator 20 is provided in such a manner so as to be continuous to the shroud 30.

The control unit 7 includes an electronic control unit 37, a fuel cartridge 38, the storage battery 39 as a power source for the electronic control unit 37, and a manually operated controller 40 for arbitrarily operating the electronic control unit 37. The electronic control unit 37, the fuel cartridge 38, and the storage battery 39 are contained in a control box 41. The fuel cartridge 38 is filled with a fuel such as benzine, alcohol, or LPG A fuel outlet of the fuel cartridge 38 is connected to a fuel inlet of the fuel-air mixer 27 via a fuel conduit 42. A fuel adjuster 44 for adjusting a flow rate of fuel is interposed in the fuel conduit 42. An ignition plug 45 is provided in the combustion housing 25 at a position adjacent to the mixer 27.

The power cylinder unit 8 includes a power cylinder 47 pivotably connected to one of the thigh portion 2 and the shank portion 4, and a power piston 48 pivotably connected to the other of the thigh portion 2 and the shank portion 4 while slidably inserted in the power cylinder 47. An operation chamber 49 defined in the power cylinder 47 by means of the power piston 48 is communicated to the compression chamber 12 of the displacer unit 6 via the pressure conduit 22.

A bending/stretching sensor 51 (that is, a power piston sensor) for detecting a bending/stretching angle between both the thigh portion 2 and the shank portion 4 is mounted therebetween. An output signal from the bending/stretching sensor 51 and output signals from the manually operated controller 40 and the displacer piston sensor 21 are inputted into the electronic control unit 37. On the basis of these signals, the electronic control unit 37 controls the actuator 20 and the fuel adjuster 44.

Examples of the actuators 20 will be described with reference to FIGS. 3 to 5.

Figure 3:
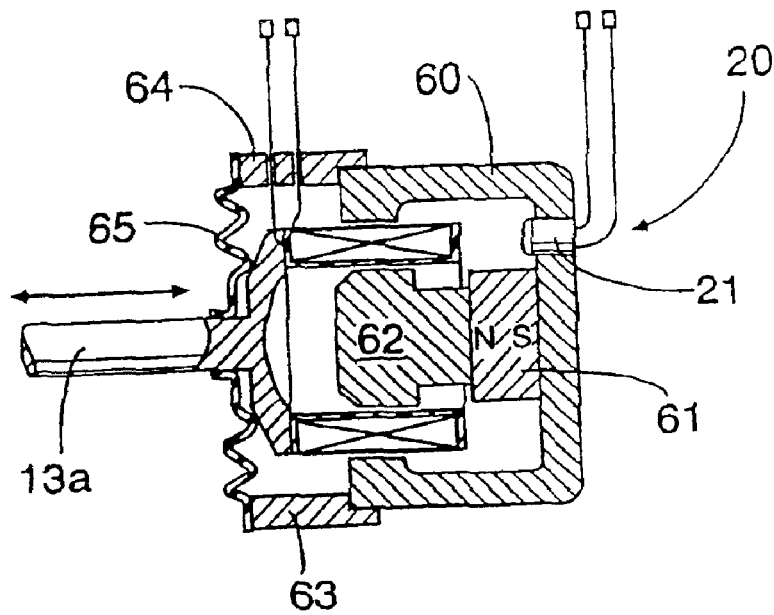
FIG. 3 is a vertical sectional view showing an example of an actuator for the Stirling engine.

The actuator 20 shown in FIG. 3 is configured as a voice coil motor. A magnet 61 is fixed on an inner end wall of a cylindrical yoke 60 with its bottom closed. A cylindrical movable coil 63, which is movable in the axial direction, is provided so as to surround a magnetic pole piece 62 connected to a leading end of the magnet 61. A rod 13a connected to the displacer piston 13 is connected to the cylindrical movable coil 63. An annular lead wire holder 64 is connected to an open end of the yoke 60, and a diaphragm 65 is stretched between the lead wire holder 64 and the rod 13a. A stroke sensor for detecting a position of the movable coil 63, which functions as a displacer piston sensor 21, is provided on an end wall of the yoke 60.

With this configuration, by repeatedly switching a direction along which current is applied to the movable coil 63, the displacer piston 13 can be reciprocated via the rod 13a by an interaction between a magnetic force generated from the movable coil 63 and a magnetic force of the magnet 61.

Figure 4:
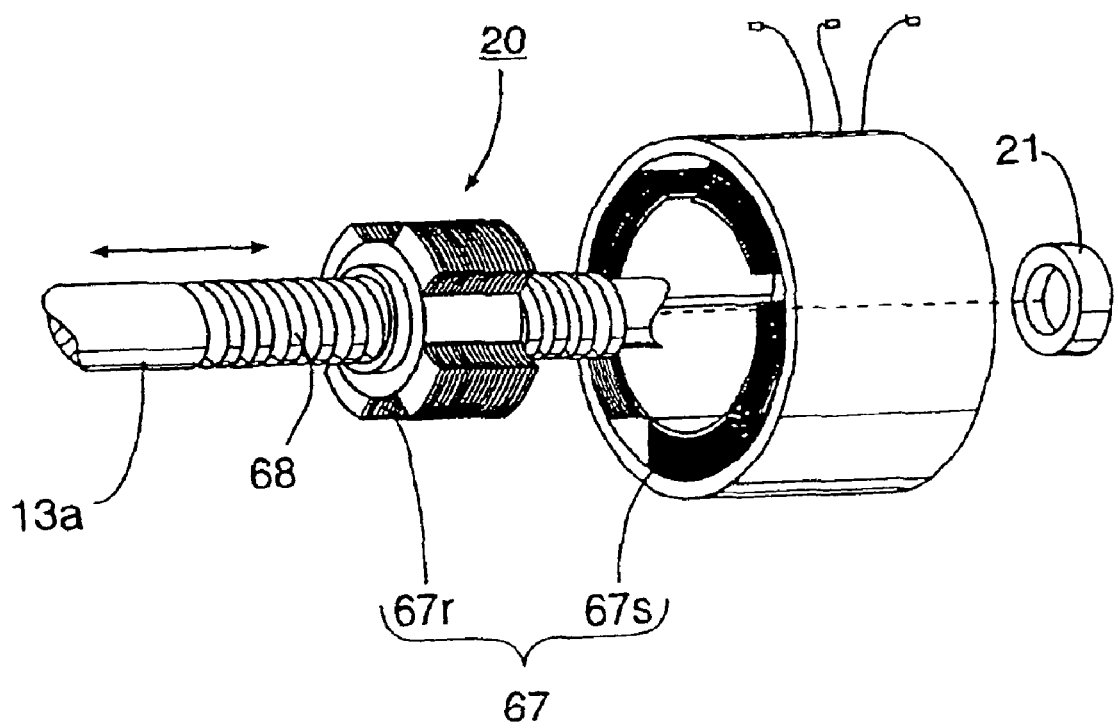
FIG. 4 is a perspective view showing another example of the actuator.

The actuator 20 shown in FIG. 4 is configured by connecting the rod 13a to a rotor 67r of a normally/reversely rotatable electric motor 67 via a ball screw 68. In this case, the rotation of the rod 13a is prohibited by rotation-stop means (not shown). An encoder for detecting an angular position of rotation of the rotor 67r, which functions as the displacer piston sensor 21, is provided on a stator 67s of the electric motor 67.

With this configuration, the displacer piston 13 can be reciprocated via the rod 13a by repeating normal rotation and reverse rotation of the rotor 67r of the electric motor 67.

Figure 5:
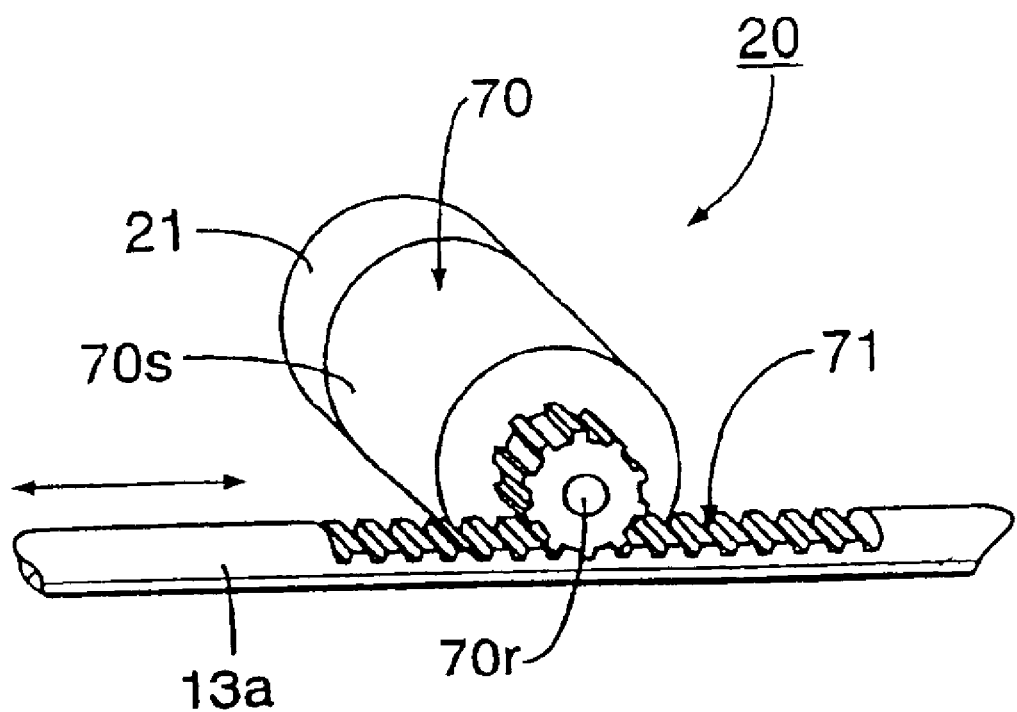
FIG. 5 is a perspective view of a further example of the actuator.

The actuator 20 shown in FIG. 5 is configured such that the rod 13a is connected to a rotor shaft 70r of a normally/reversely rotatable electric motor 70 via a rack/pinion mechanism 71. Even in this case, an encoder for detecting an angular position of rotation of the rotor shaft 70r, which functions as the displacer piston sensor 21, is provided on a stator 70s of the electric motor 70.

With this configuration, the displacer piston 13 can be reciprocated via the rod 13a by repeating normal rotation and reverse rotation of the rotor shaft 70r of the electric motor 70.

The function of the first embodiment will be described below.

Fuel is fed from the fuel cartridge 38. The flow rate of the fuel is adjusted by the fuel adjuster 44. The fuel is then supplied to the fuel-air mixer 27, to be mixed with air which has flown from the air intake port 31 into the fuel-air mixer 27 via the air passage 32. The air-fuel mixture is ignited once by the ignition plug 45, and thereafter, the combustion of the air-fuel mix is continuously accelerated by the catalyst 26, to heat the expansion chamber 11 from the head portion side of the displacer cylinder 10 at a specific high temperature. An exhaust gas generated by the combustion is discharged to the outside through the exhaust pipe 28.

The radiator 15 keeps the compression chamber 12 in a specific low temperature state. The heat regenerator 17 receives heat from a working gas which is moving between the expansion chamber 11 and the compression chamber 12 via the communication port 16.

The control actuator 20 is operated on the basis of a command from the electronic control unit 37, to reciprocate the displacer piston 13, thereby generating a pressure amplitude in the compression chamber 12. The pressure is transmitted to the operation chamber 49 of the power cylinder 47 via the flexible pressure conduit 22, to reciprocate the power piston 48, thereby bending/stretching the shank portion 4 relative to the thigh portion 2. The bending/stretching motion of the shank portion 2 relative to the thigh portion 4 assists the walking of the user.

At this time, to efficiently drive the power piston 48, the electronic control unit 37 identifies a position of the power piston 48 on the basis of an output signal from the bending/stretching sensor 51, and operates the control actuator 20 such that the displacer piston 13 is in advance of the power piston 48 by a converted crank angle of 90°. Further, the electronic control unit 37 can control the operational speed of the displacer piston 13 from zero to an arbitrary value so as to control the bending/stretching speed of the shank portion 4 relative to the thigh portion 2 from zero to an arbitrary value. With this configuration, the prosthetic leg 1 can be moved on the basis of the user's intention.

Since the combustion form in the catalyst type combustor 14 is continuous combustion, it is possible to enhance a combustion efficiency and to eliminate any combustion oscillation. In addition, since the fuel cartridge 38 is adopted, it is possible to rapidly supplement fuel and also to operate the drive unit for assisting the walking of the user for a long time.

Since power consumption of the storage battery 39 as the power source for the electronic control unit 37 is very small and a further part of heat generated by the combustor 14 is converted into an electric energy by the thermal-electric converting device 34 to be stored in the storage battery 39, the useful life of the storage battery becomes longer.

Since only the power cylinder unit 8 is provided on the prosthetic leg 1 while the relatively heavy displacer unit 6, the fuel cartridge 38, the electronic control unit 37, etc. are mounted on the belt B worn around the user's waist portion, and the displacer unit 6 is connected to the power cylinder unit 8 via the flexible pressure conduit 22, it is possible to make the prosthetic leg 1 lightweight and slim while ensuring the smooth bending/stretching motion of the prosthetic leg 1. The prosthetic leg 1 also allows the user to easily, rapidly, and simply mount/dismount the displacer unit 6 by mounting/dismounting the belt B around the waist portion of the user.

As described above, the displacer unit 6 and the power cylinder unit 8 can be disposed separately from each other. More specifically, they can be freely disposed at desired positions. As a result, it is possible to increase the degree of freedom in layout of the Stirling engine and enhance the applicability of the Stirling engine. For example, it is possible to apply the Stirling engine to drive means for driving an object other than the prosthetic leg 1. Also, the power piston 48 can freely be remote-controlled by controlling a phase and an operating speed of the displacer piston 13 by the control actuator 20.

Figure 6:
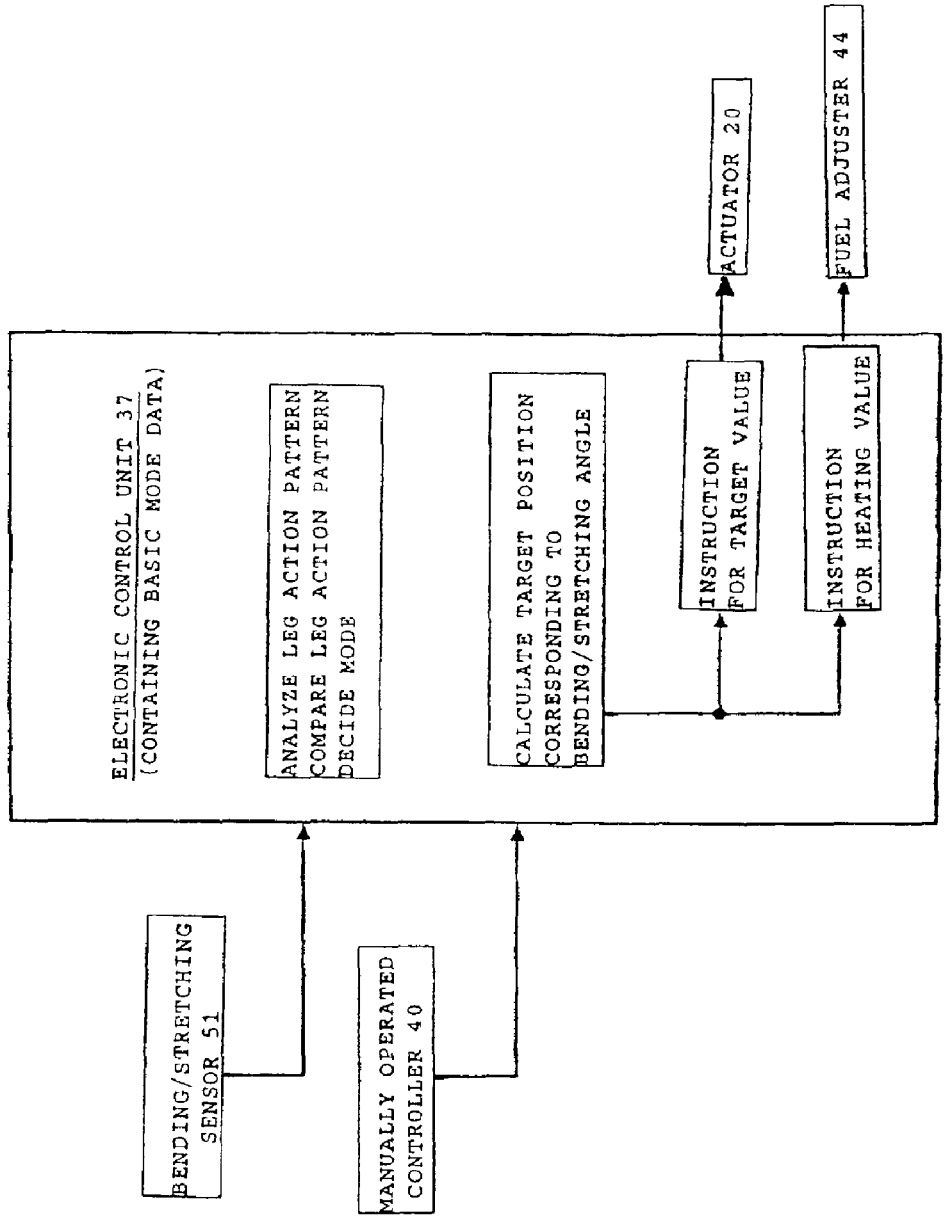
FIG. 6 is a flow diagram showing a control system of the Stirling engine.

The control of the prosthetic leg 1 will be more fully described with reference to FIG. 6. When receiving a detection signal from the bending/stretching sensor 51, the electronic control unit 37 decides a leg action pattern such as a walking, running, slope ascending, slope descending, stair ascending, or stair descending pattern and decides a leg stroke such as a standing, resting, grounding, or a kicking stroke by comparison with a basic leg action pattern, calculates a target bending/stretching position corresponding to the detection signal from the bending/stretching sensor 51 with reference to basic mode data, and outputs the calculated result to the actuator 20 as a target value. At the same time, the electronic control unit 37 calculates heat which corresponds to the target value and is to be generated by the combustor 14 and outputs a control signal to the fuel adjuster 44.

The manually operated controller 40 changes a phase difference between the displacer piston 13 and the power piston 48, and gives an instruction to start/stop the whole system to the electronic control unit 37. In particular, when the prosthetic leg 1 is intended to move up or down to or from a step portion larger than that of a usual stair, the manually operated controller 40 outputs a signal for instructing an increase/decrease in the bending/stretching angle.

Figure 7:
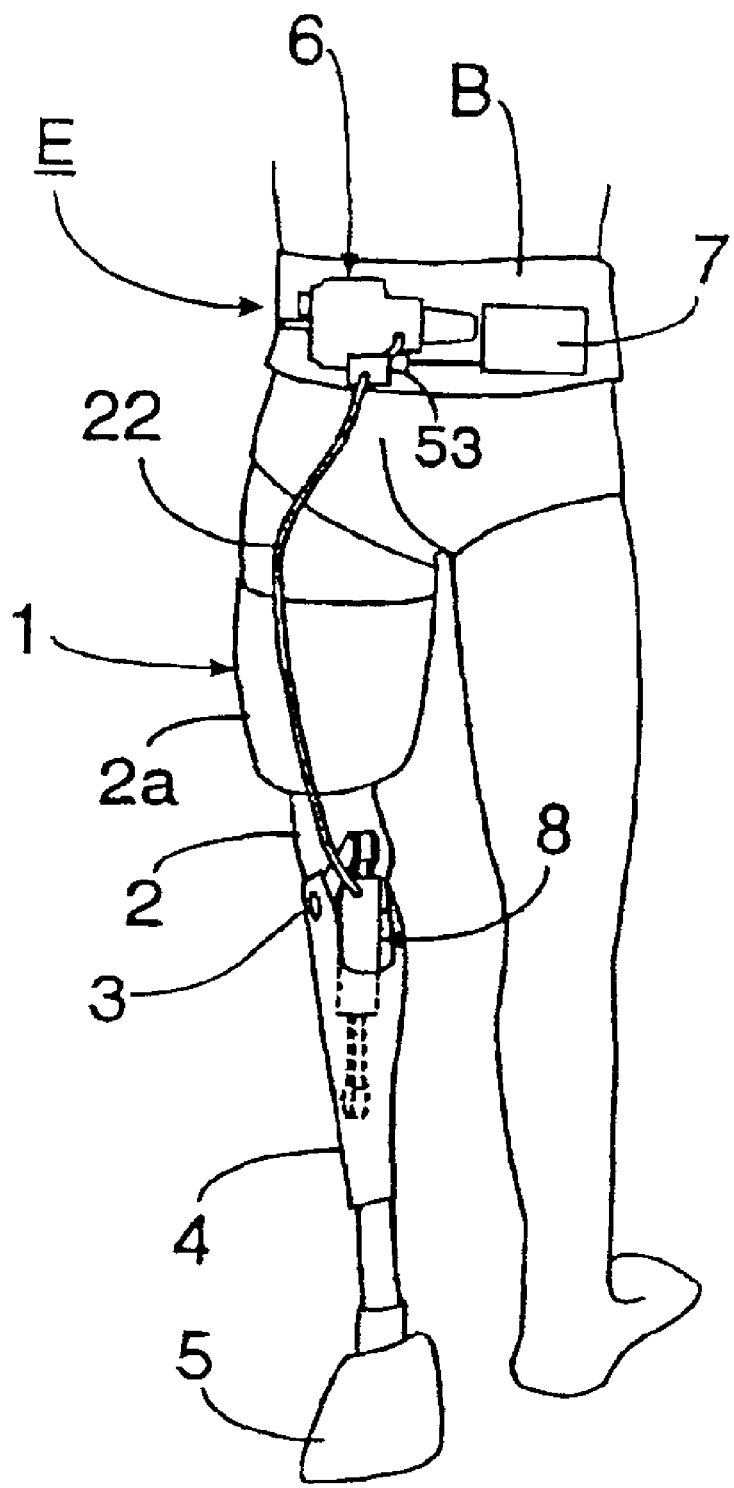
FIG. 7 is a schematic view showing a second embodiment of the present invention, corresponding to FIG. 1.

A second embodiment of the present invention shown in FIG. 7 will be described below. According to the second embodiment, a hydraulic converter 53 for converting the pressure in the compression chamber 12 into a hydraulic pressure is provided on the displacer unit 6. An output port of the hydraulic converter 53 is connected to the operation chamber 49 of the power cylinder 47 via the pressure conduit 22. The other configurations are the same as those of the first embodiment, and therefore, parts in FIG. 3 corresponding to those in the first embodiment are designated by the same reference numerals and the overlapped description thereof is omitted.

According to the second embodiment, since the pressure in the compression chamber 12 of the displacer unit 6 is converted into a hydraulic pressure by the hydraulic converter 53, and the hydraulic pressure is transferred to the operation chamber 49 of the power cylinder 47. Thus, it is possible to eliminate the occurrence of elastic compression, which has been caused for a working gas, in the pressure conduit 22 and the operation chamber 49, and hence to improve a pressure transmission efficiency. Further, since the pressure conduit 22 is filled with a non-compressive fluid, it is possible to eliminate a possibility that the inner volume of the pressure conduit 22 becomes a dead volume of the Stirling engine E, and hence to improve a theoretical efficiency of the Stirling engine E.

Figure 8:
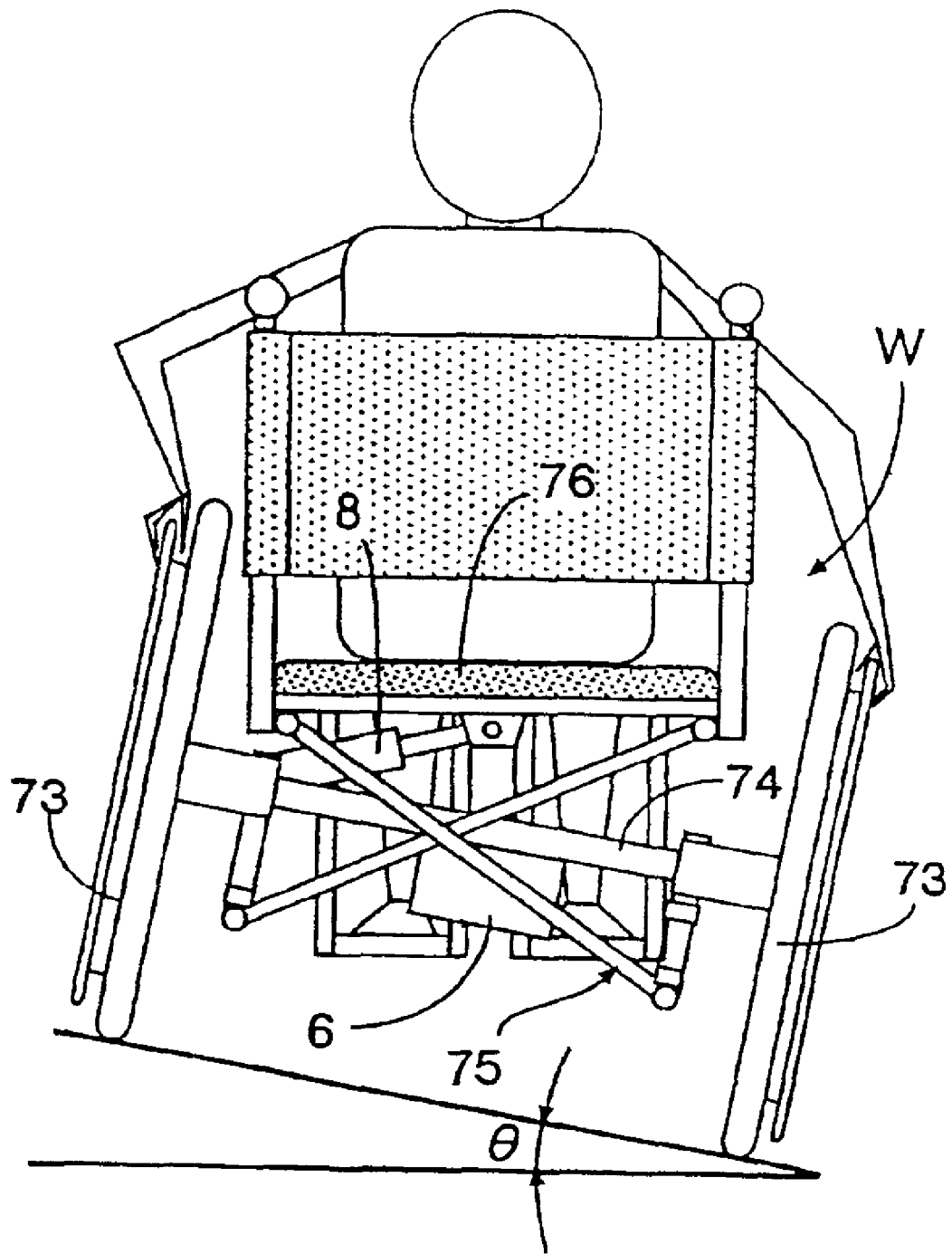
FIG. 8 is a front view of a wheelchair according to a third embodiment of the present invention.

A third embodiment shown in FIG. 8 will be described below. In the third embodiment, a Stirling engine E is used for controlling a posture of a seat of a wheelchair W. In the wheelchair W, a seat 76 is connected via an X-type link mechanism 75 to a frame 74 for supporting a wheel 73. A displacer unit 6 of the Stirling engine E is mounted to a back surface of the frame 74, and a power piston 48 and a power cylinder 47 of a power cylinder unit 8 are connected to the frame 74 and the seat 76, respectively. An inclination sensor (not shown) is mounted to the seat 76. On the basis of an output signal from the sensor, an actuator 20 of the displacer unit 6 is operated in such a manner that an inclination angle of the seat 76 becomes zero, to drive the power piston 48. With this posture control of the seat, it is possible to usually keep the seat 76 in a horizontal state irrespective of the inclination of a road surface, and hence to improve the seating comfort, and also it is possible to realize a long-time drive while suppressing an increase in weight of the wheelchair W by using the Stirling engine E.

A fourth embodiment of the present invention shown in FIG. 9 will be described below. A power piston 48 of the Stirling engine E drives a power generator 81 via a crank mechanism 80. An output side of the power generator 81 is connected to a load apparatus 83 such as a battery or an electric motor via load adjusting means 82. The load adjusting means 82, which is adapted to adjust a load applied to the load apparatus 83, is controlled by the electronic control unit 37 on the basis of detection signals from a displacer piston sensor 21 and a power piston sensor 51.

Figure 9:
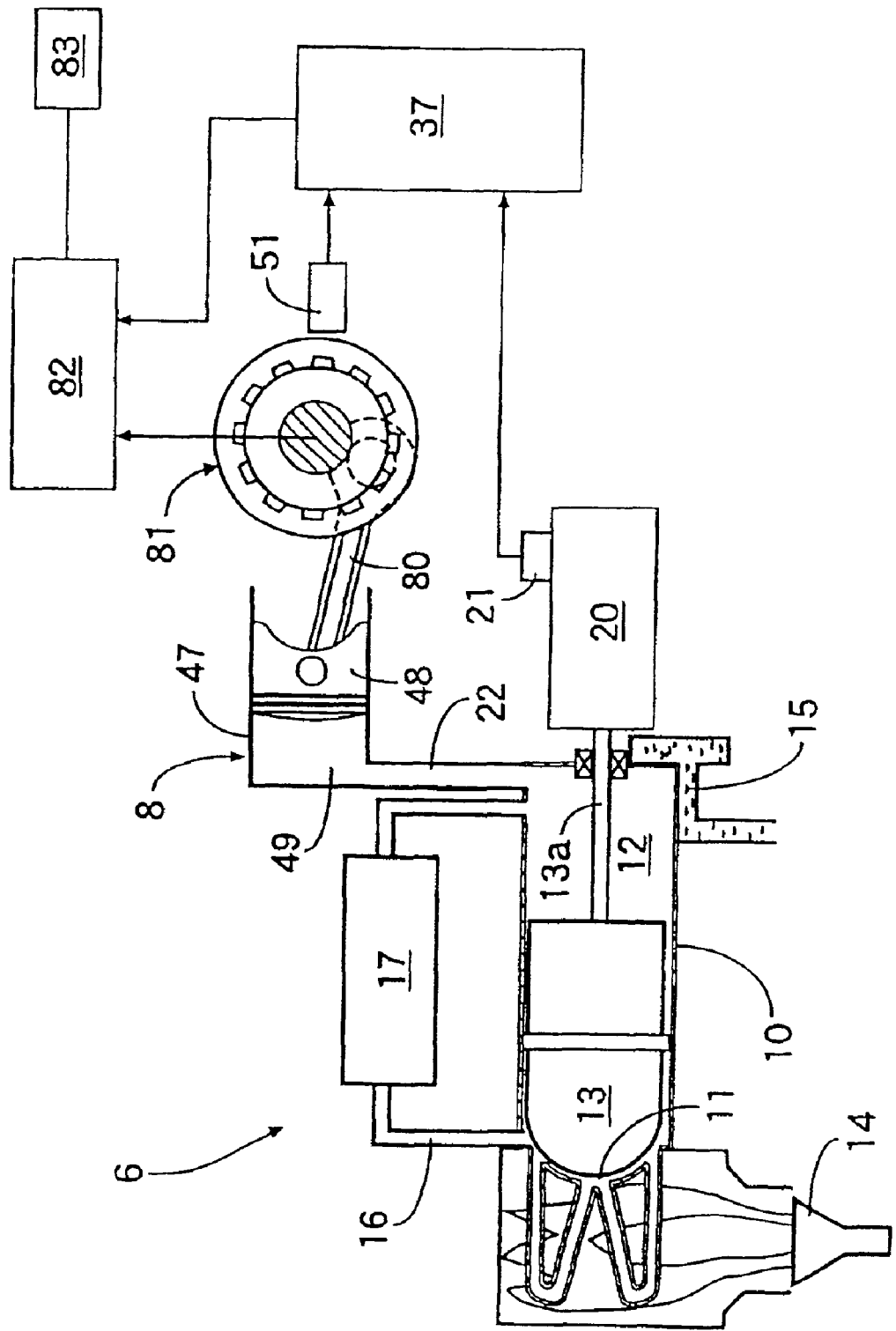
FIG. 9 is a vertical sectional view of a Stirling engine according to a fourth embodiment of the present invention.

The other configurations are the same as those of the Stirling engine according to the first embodiment, and therefore, parts in FIG. 9 corresponding to those in the Stirling engine E according to the first embodiment are designated by the same reference numerals and the overlapped description thereof is omitted.

According to the fourth embodiment, even if heat generated by the combustor 14 of the displacer unit 8 is somewhat varied, the output from the power piston 48 can be stabilized.

Figure 10:
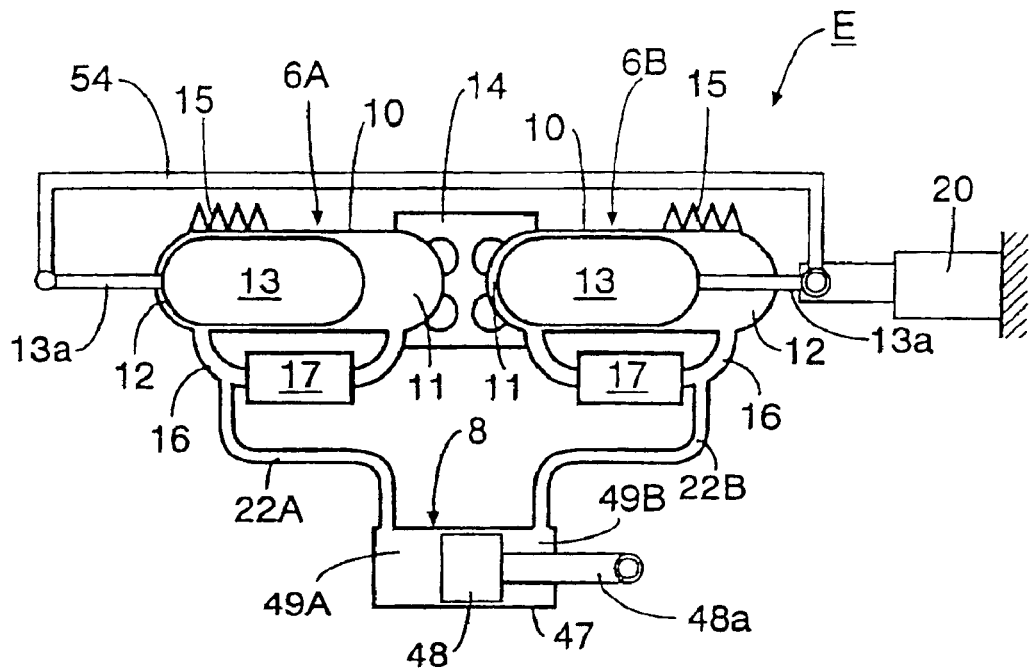
FIG. 10 is a vertical sectional view of a Stirling engine according to a fifth embodiment of the present invention.

A fifth embodiment of the present invention shown in FIG. 10 will be described below. A Stirling engine E according to the fifth embodiment includes a pair of displacer units 6A and 6B and a single double-acting type power cylinder unit 8. The pair of displacer units 6A and 6B are disposed in a state in which head portions of displacer cylinders 10 of the displacer units 6A and 6B are opposed to each other. A common combustor 14 for heating both the head portions of the displacer cylinders 10 is provided so as to surround both the head portions of the displacer cylinders 10. Rods 13a of displacer pistons 13 of both the displacer units 6A and 6B are integrally connected to each other via a connection link 54 and also connected to a common control actuator 20. In this case, a phase difference of 90°, which is a value converted in a crank angle, is given between the displacer pistons 13 of the displacer units 6A and 6B. The other configurations of each of the displacer units 6A and 6B is the same as those of the displacer unit 6 in the first embodiment, and therefore, parts shown in FIG. 10 corresponding to those described in the first embodiment are designated by the same reference numerals and the overlapped description thereof is omitted.

The double-acting type power cylinder unit 8 includes a power cylinder 47 with both ends closed, and the inside of the power cylinder 47 is partitioned into first and second operation chambers 49A and 49B by a power piston 48 fitted in the power cylinder 47. These first and second operation chambers 49A and 49B are connected to compression chambers 12 of the first and second displacer units 6A and 6B via flexible first and second pressure conduits 22A and 22B, respectively. An output rod 48a of the power piston 48 passes through one end wall of the power cylinder 47, and drives a load (not shown).

With this configuration, when the displacer pistons 13 of the first and second displacer units 6A and 6B are simultaneously reciprocated by the control actuator 20 via the connection link 54, pressure amplitudes are alternately generated in the compression chambers 12 of the displacer units 6A and 6B, so that the first and second operation chambers 49A and 49B in the power cylinder 47 are alternately boosted, to drive the power piston 48 in the reciprocating directions.

Even in the fifth embodiment, both the first and second displacer units 6A and 6B and the power cylinder unit 8 can be disposed separately from each other and also displaced relative to each other. Further, the motion of the power piston 48 of the power cylinder unit 8 can be freely remote-controlled by controlling the phases and operation speeds of both the displacer pistons 13 by the control actuator 20.

A sixth embodiment of the present invention shown in FIG. 11 will be described below. The sixth embodiment has the same configuration as that of the fifth embodiment shown in FIG. 10, except that first and second displacer units 6A and 6B are disposed in parallel with their head positions of the displacer cylinders 10 directed in the same direction, and rods 13a of displacer pistons 13 are connected to both ends of an I-type lever 56 swingably supported by a fixed pivot 55 via links 57 and a common actuator 20 is connected to one end of the lever 56. It is to be noted that parts corresponding to those in the fifth embodiment are designated by the same reference numerals and the overlapped description thereof is omitted.

A seventh embodiment of the present invention shown in FIGS. 12(a), 12(b) and 12(c) will be described below. First and second displacer units 6A and 6B are disposed in parallel with head portions of the displacer cylinders 10 directed in the same direction. First and second control actuators 20A and 20B, which are individually operable, are connected to displacer pistons 13 of the displacer units 6A and 6B, respectively.

First and second power cylinder units 8A and 8B are disposed in parallel so as to correspond to the first and second displacer units 6A and 6B, respectively. Operation chambers 49 of the power cylinder units 8A and 8B are connected to compression chambers 12 of the first and second displacer units 6A and 6B via first and second pressure conduits 22A and 22B, respectively.

Each of the first and second power cylinder units 8A and 8B is of a single-acting type, and an operational member 59 is connected to output rods 48a of power pistons 48 of the first and second power cylinder units 8A and 8B via links 58.

Figure 11:
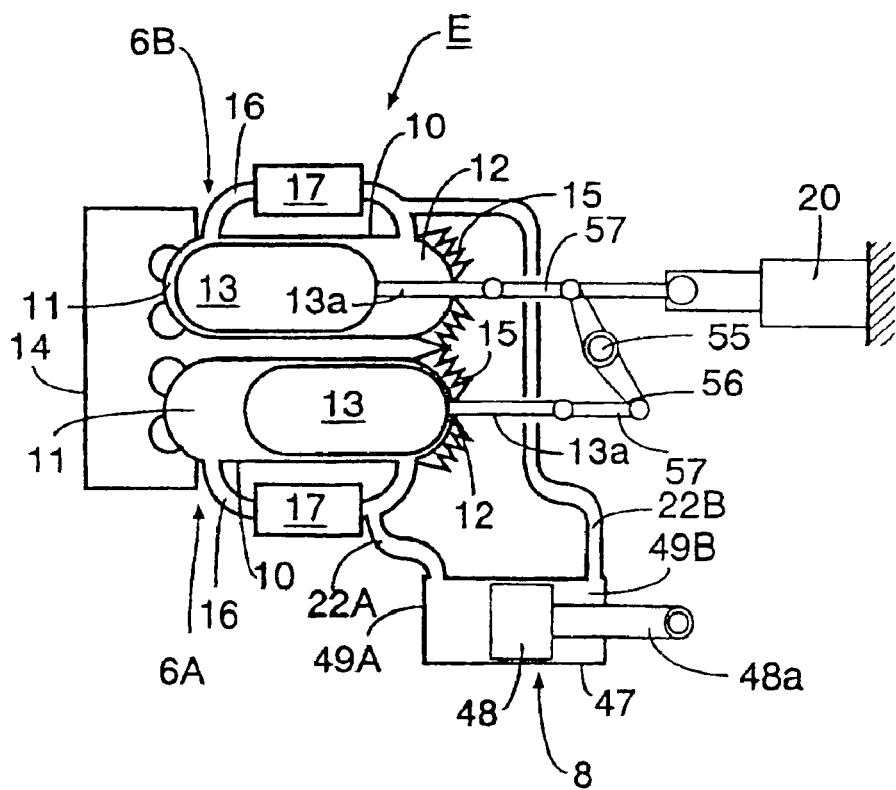
FIG. 11 is a vertical sectional view of a Stirling engine according to a sixth embodiment of the present invention.

In FIGS. 12(a), 12(b) and 12(c), parts of the first and second displacer units 6A and 6B, corresponding to those in the sixth embodiment shown in FIG. 11, are designated by the same reference numerals and the overlapped description thereof is omitted.

According to the seventh embodiment, as shown in FIGS. 12(a), 12(b) and 12(c), by individually operating the first and second control actuators 20A and 20B at suitable times, the power pistons 48 of the first and second power cylinder units 8A and 8B can be alternately operated with a phase difference of 90°, which is a value converted in crank angle, given therebetween, the phases of the power pistons 48 can be changed, and the operational member 59 can be swung or translated. Accordingly, it is possible to realize a complicated action of the operational member 59.

While not shown in FIGS. 10 to 12(c), the Stirling engine E in each of the fifth to seventh embodiments includes the same displacer piston sensor 21, power piston sensor 51, and control unit 37 as those described in the first embodiment.

The present invention is not limited to the above-described embodiments, and it is to be understood that various changes in design may be made without departing from the scope of the present invention.

As described above, according to the first feature of the present invention, there is provided a Stirling engine including a displacer unit in which a displacer piston is slidably fitted in a displacer cylinder so as to partition the inside of the cylinder into an expansion chamber and a compression chamber, and a power cylinder unit in which a power piston is slidably fitted in a power cylinder so as to form an operation chamber in communication with the compression chamber in the cylinder. The displacer unit and the power cylinder unit are disposed separately from each other. The compression chamber is connected to the operation chamber via a pressure conduit. A control actuator, capable of arbitrarily controlling the displacer piston, is connected to the displacer piston. With the first feature, the displacer unit and the power cylinder unit can be disposed separately from each other, more specifically, freely disposed at desired positions. As a result, it is possible to increase the degree of freedom in layout of the Stirling engine and thereby to enhance the applicability of the Stirling engine. Further, the power piston of the power cylinder unit can be freely remote-controlled by controlling a phase and an operating speed of the displacer piston by means of the control actuator.

According to the second feature of the present invention, in addition to the first feature, the pressure conduit has flexibility. With this second feature, the displacer unit and the power cylinder unit can be displaced relative to each other by the flexibility of the pressure conduit, so that the displacer unit and the power cylinder unit can be disposed without interference therebetween. As a result, it is possible to further increase the degree of freedom in layout of the Stirling engine and hence to further enhance the applicability of the Stirling engine.

According to the third feature of the present invention, a hydraulic converter for converting a pressure in the compression chamber to a hydraulic pressure and transmitting the hydraulic pressure to the operation chamber is provided between the compression chamber and the pressure conduit. With this third feature, since a pressure of the compression chamber of the displacer unit is converted into a hydraulic pressure by the hydraulic converter and the hydraulic pressure is transmitted to the operation chamber, elastic compression, which is liable to occur in the case of using a working gas as a transmission medium, does not occur in both the pressure conduit and the operation chamber. Thus, it is possible to improve a pressure transmission efficiency. Further, since the pressure conduit is filled with a non-compressive fluid, it is possible to eliminate a possibility that an inner volume of the pressure conduit becomes a dead volume of the Stirling engine, and hence to improve a theoretical efficiency of the Stirling engine.

As described above, according to the fourth feature of the present invention, there is provided a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber communicated to the compression chamber in the cylinder. The control system includes a displacer piston driving means for driving the displacer piston, a displacer piston position detecting means for detecting a position of the displacer piston, a power piston position detecting means for detecting a position of the power piston and a control unit for controlling an operation of the displacer driving means on the basis of detection signals from both piston position detecting means. With this feature it is possible to control the motion of the power piston with a high responsiveness by operating the displacer piston at a suitable time by the displacer driving means, and hence to increase the applicability of the Stirling engine. In particular, since the operation of the displacer driving means is controlled by the control unit on the basis of detection signals from the displacer piston position detecting means and the power piston position detecting means, it is possible to freely control the operation, stoppage, an operating speed, and a stopped position of the power piston irrespective of heat generated by the heating portion of the displacer unit.

According to the fifth feature of the present invention, in addition to the fourth feature, the displacer piston driving means is operated by the control unit so as to change a difference in phase between the displacer piston and the power piston. With this second feature, it is possible to freely control an operating timing and a stopping timing of the power piston.

According to the sixth feature of the present invention, there is provided a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder. The control system being includes a displacer piston driving means for driving the displacer piston, a heat control means for controlling heat generated by a heating portion of the displacer cylinder, a displacer piston position detecting means for detecting a position of the displacer piston, a power piston position detecting means for detecting a position of the power piston and a control unit for controlling an operation of the heat control means on the basis of detection signals from both piston position detecting means.

With this sixth feature, it is possible to control the motion of the power piston with a high responsiveness by operating the displacer piston at a suitable time by the displacer driving means, and hence to increase the applicability of the Stirling engine. In particular, since the operation of the heat control means for controlling heat generated by the heating portion of the displacer cylinder is controlled by the control unit on the basis of detection signals from the displacer piston position detecting means and the power piston position detecting means, it is possible to efficiently use heat generated by the heating portion.

According to a seventh feature of the present invention, there is provided a control system for a Stirling engine including a displacer unit in which a displacer piston is slidably fitted in a displacer cylinder so as to partition the inside of the cylinder into an expansion chamber and a compression chamber. A power cylinder unit is provided in which a power piston is slidably fitted in a power cylinder so as to form an operation chamber in communication with the compression chamber in the cylinder. The control system includes a displacer piston driving means for driving the displacer piston, a load adjusting means for adjusting a load of a load apparatus connected to the power piston, a displacer piston position detecting means for detecting a position of the displacer piston, a power piston position detecting means for detecting a position of the power piston and a control unit for controlling an operation of the load adjusting means on the basis of detection signals from both piston position detecting means.

With this fourth feature, it is possible to control the motion of the power piston with a high responsiveness by operating the displacer piston at a suitable time by the displacer driving means, and hence to increase the applicability of the Stirling engine. In particular, since the operation of the load adjusting means is controlled by the control unit on the basis of detection signals from the displacer piston position detecting means and the power piston position detecting means, it is possible to stabilize the output from the power piston even if the heat generated by the heating portion is somewhat varied.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a walking movement of a user and is operatively connected to said displacer piston for arbitrarily controlling the movement of said displacer piston to impart said walking movement operation to said operation chamber.

2. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a running movement of a user and is operatively connected to said displacer piston for arbitrarily controlling the movement of said displacer piston to impart said running movement operation to said operation chamber.

3. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a slope ascending movement of a user and is operatively connected to said displacer piston for arbitrarily controlling the movement of said displacer piston to impart said slope ascending movement operation to said operation chamber.

4. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a slope descending movement of a user and is operatively connected to said displacer piston for arbitrarily controlling the movement of said displacer piston to impart said slope descending movement operation to said operation chamber.

5. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a stairs ascending movement of a user and is operatively connected to said displacer piston for arbitrarily controlling the movement of said displacer piston to impart said stairs ascending movement operation to said operation chamber.

6. A Stirling engine including a displacer unit in which a displacer piston is slidably fitted in a displacer cylinder for partitioning an interior portion of said cylinder into an expansion chamber and a compression chamber, and a power cylinder unit having a power piston slidably fitted in a power cylinder for forming an operation chamber in communication with said compression chamber in said cylinder comprising:

said displacer unit and said power cylinder unit are disposed separately from each other;

said compression chamber is connected to said operation chamber via a pressure conduit; and a control actuator determines a stairs descending movement of a user and is operatively connected to said displacer piston for arbitrarily controlling the movement of said displacer piston to impart said stairs descending movement operation to said operation chamber.

7. The Stirling engine according to claim 1, wherein said pressure conduit has flexibility.

8. The Stirling engine according to claim 1, wherein a hydraulic converter is operatively connected to said compression chamber for converting a pressure in said compression chamber to a hydraulic pressure and transmitting the hydraulic pressure to said operation chamber, said hydraulic converter being provided between said compression chamber and said pressure conduit.

9. The Stirling engine according to claim 1, wherein a hydraulic converter is operatively connected to said compression chamber for converting a pressure in said compression chamber to a hydraulic pressure and transmitting the hydraulic pressure to said operation chamber, said hydraulic converter being provided between said compression chamber and said pressure conduit.

* * * * *